United States Patent [19]

Grisar et al.

[11] 4,038,412

[45] July 26, 1977

[54] N-(PHENYLETHER-SUBSTITUTED BENZYL)ALKANEDIAMINES

[75] Inventors: J. Martin Grisar; George P. Claxton, both of Cincinnati, Ohio

[73] Assignee: Richardson-Merrell Inc., Wilton, Conn.

[21] Appl. No.: 607,333

[22] Filed: Aug. 25, 1975

[51] Int. Cl.² .......................... A01N 9/20; C07C 87/28
[52] U.S. Cl. ............................. 424/280; 260/326 R; 260/343.7; 260/501.18; 260/501.19; 260/501.2; 260/566 A; 260/566 F; 260/520.9; 260/592; 260/599; 260/600 R; 424/316; 424/330

[58] Field of Search .................... 260/570.5 P, 343.7, 260/501.18, 501.19, 501.2; 424/288, 316, 330

[56] References Cited

U.S. PATENT DOCUMENTS 3,872,171  3/1975  Cronin et al. .................. 260/570.5 X

*Primary Examiner*—Robert V. Hines
*Attorney, Agent, or Firm*—William J. Stein; George W. Rauchfuss, Jr.; Eugene O. Retter

[57] ABSTRACT

Novel N-(substituted benzyl)alkanediamines are prepared which are useful for the prevention and inhibition of viral infections.

9 Claims, No Drawings

N-(PHENYLETHER-SUBSTITUTED BENZYL)ALKANEDIAMINES

FIELD OF THE INVENTION

This invention relates to new organic chemical compounds, to their preparation, and to pharmaceutical compositions containing the same. The compounds described herein are useful in inactivating or inhibiting viruses by their administration to either an infected or a non-infected host. Additionally, these compounds are useful as immunosuppressants and as inhibitors of blood platelet aggregation.

BACKGROUND OF THE INVENTION

The effective control of virus diseases is primarily achieved, at present, by means of immunization vaccines. For, example, polimyelitis, smallpox, measles and influenza are well recognized diseases in which viral vaccines have proven effective. In general, however, viral vaccines have had only a moderate success in animal prophylaxis. Each vaccine acts primarily against a specific virus and is not heterophilic in the protection it offers. Hence, vaccines have not provided a practical solution against the wide array of infectious viruses, even when limited as for example, solely to respiratory viruses.

One approach to the control of virus-related diseases and, particularly to the spread of such virus diseases, has been to search for medicinal agents or chemotherapeutic agents which are capable of inhibiting the growth of viruses, thereby preventing the spread of disease as well as preventing further damage to cells and tissues of the animal host which have not as yet been infected. Heretofore, only a limited number of virus infections such as smallpox, Asian influenza and herpes keratitis have been prevented by chemical antiviral agents. Sulfonamides and antibiotics which have revolutionized the treatment of bacterial infections have substantially no effect upon virus infections. Certain infections caused by large viruses, such as lymphogranuloma venereum, psittacosis and trachoma have been successfully treated using antibiotics and sulfa drugs. However, the majority of infections have not been responsive to attack by chemotherapeutic agents. Thus, it can be seen that there is a need for new chemotherapeutic agents which are effective against a broad range of virus diseases, and which at the same time, are non-toxic to the host.

As a result of a long series of investigations, applicants have discovered a novel class of N-(substituted benzyl)alkanediamines which are particularly useful anti-viral agents. These compounds are effective against a wide spectrum of virus infections and can be utilized in treating such infections either prophylactically or therapeutically.

To applicants' knowledge, the compounds described and claimed herein are novel compounds which have not been described nor reported in the literature. Moreover, these compounds belong to a class of N-(substituted benzyl)alkanediamines heretofor unknown to possess antiviral activity. They possess a wide spectrum of antiviral activity in varying degrees which could not have been predicted from a knowledge of the present state of the art.

SUMMARY OF THE INVENTION

This invention relates to new derivatives of N-(substituted benzyl)alkanediamines, to their preparation, compositions thereof and to their use as pharmaceutical agents. More particularly, the compounds of the present invention relate to phenylalkyl and phenoxyalkyl ethers, thioethers and sulfones of (benzyl)alkanediamines.

Still more particularly, the compounds of the present invention may be represented by the following general formula:

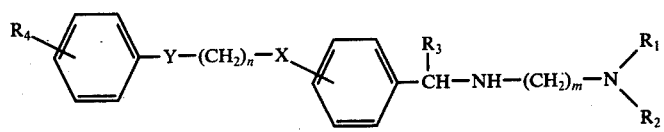

(I)

wherein $R_1$, $R_2$, $R_3$ and $R_4$ are each selected from the group consisting of hydrogen and loweralkyl; X is selected from the group consisting of oxygen, sulfur and sulfonyl; Y is oxygen or a sigma bond, $m$ is an integer of from 2 to 4; $n$ is an integer of from 1 to 4 with the proviso that when Y is oxygen, then $n$ cannot be 1; and the pharmaceutically acceptable acid addition salts thereof.

The compounds within the scope of the present invention include both the free base form as well as the pharmaceutically acceptable acid addition salts thereof. Generally, the salts of these compounds are crystalline materials which are soluble in water and various hydrophilic solvents, and which, in comparison to their free base forms, possess higher melting points and an increased stability.

DETAILED DESCRIPTION OF THE INVENTION

As can be seen from general formula (I) above, the N-(substituted benzyl)alkanediamines of the present invention consist of an alkanediamine moiety and a substituted benzyl moiety. The benzyl moiety may be optionally substituted on the phenyl ring with either a phenylalkyl or penoxyalkyl ether, thioether or sulfone side chain.

The terminal nitrogen atom of the alkanediamine moiety may remain unsubstituted, as when the symbols $R_1$ and $R_2$ are hydrogen, resulting in primary amines. Additionally, the terminal nitrogen can be either mono or di-substituted with a loweralkyl group, resulting in the corresponding secondary and tertiary amines. The term loweralkyl as applied throughout the specification relates to straight or branched chain alkyl groups having from 1 to 4 carbon atoms. Illustrative of such groups are the methyl, ethyl, n-propyl, isopropyl, n-butyl, sec-butyl and tert-butyl radicals.

The alkane portion of the class of alkanediamines delineated by formula (I) above is restricted by the symbol $m$ to from 2 to 4 carbon atoms. Thus, all of the compounds described herein are named as either 1,2- ethanediamines, 1,3-propanediamines or 1,4-butanediamines.

The methyl carbon atom of the benzyl moiety may

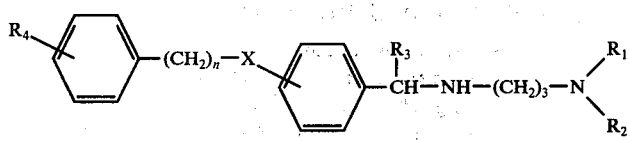

also be substituted with a loweralkyl group as indicated by the symbol $R_3$. Where $R_3$ represents the methyl radical, a preferred class of alkanediamines are obtained.

As previously mentioned, the phenyl ring portion of the benzyl moiety is mandatorily substituted by an ether, thioether or sulfone side chain. These side chains, designated by the partial structure

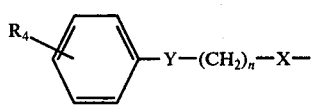

in formula (I) above, represent large lipophilic groups which have been found necessary to impart the desired properties to the compounds being claimed. Thus, when the symbol X represents an oxygen atom, a preferred subclass of ether side chains is delineated. When the symbol X represents sulfur, a thioether side chain is present; and when X represents the symbol $SO_2$, a sulfone side chain is present. These side chains may be of varying length as indicated by the symbol $n$.

These side chains are substituted on the phenyl portion of the benzyl moiety in either the ortho, meta, or para positions as indicated by the bond going from the symbol X to the center of the phenyl ring. The alkyl portion of this side chain contains from 1 to 4 carbon atoms as indicated by the symbol $n$.

The terminal portion of the side chain contains either a mandatory phenyl or phenoxy group as indicated by the symbol Y. Thus, when Y represents a sigma bond, the side chain terminates with a phenylalkyl or substituted phenylalkyl group. The expression "sigma bond" is intended to refer to the ordinary single bond linkage between two adjacent carbon atoms resulting from the overlap of their corresponding orbitals. Alternatively, when the symbol Y represents an oxygen atom, the side chain terminates in a phenoxyalkyl or substituted phenoxyalkyl moiety.

The terminal phenyl ring can either be substituted or unsubstituted, as indicated by the symbol $R_4$. Thus, when $R_4$ is hydrogen the terminal phenyl ring remains unsubstituted. Substitution is limited to that of a monosubstitution at either the ortho, meta or para positions of the phenyl ring as indicated by the bond $R_4$ going to the center of the phenyl ring. Substitution is further limited solely to that of a loweralkyl group as previously defined.

A preferred subclass of compounds within the scope of formula (I) above, are the N-(substituted benzyl)-1,3-propanediamines, in which Y is a sigma bond and the symbol $m$ is the integer 3. These compounds can be represented by the structural formula (II)

wherein the symbols $N_o$ $R_1$, $R_2$, $R_3$, $R_4$ and X have the values previously assigned. Illustrative of the species included therein are:

N-ethyl,N-methyl-N'-[[p-(3-phenylpropylthio)-phenyl]methyl]-1,3-propanediamine,

N-[α-methyl[p-(3-phenylpropylthio)phenyl]methyl]-1,3-propanediamine,

N-[α-methyl-[p-(3-(o-propylphenyl)propylthio]-phenyl]-methyl]-1,3-propanediamine, N,N-dibutyl-N'-[[p-(3-phenylpropylsulfonyl)phenyl]-methyl]-1,3-propanediamine, N-[α-methyl[p-[3-(o-methylphenyl)propylsulfonyl]-phenyl]methyl]-1,3-propanediamine, and N-[α-methyl[o-[3-(p-t-butylphenyl)propylsulfonyl]-phenyl]-N'-propyl-1,3-propanediamine.

A still more preferred group of compounds within the above subclass are the 1,3-propanediamine ethers as illustrated by the structural formula:

(III)

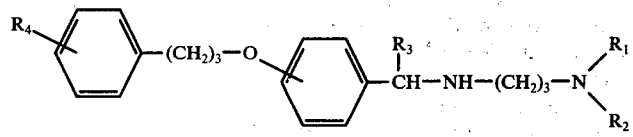

wherein the symbols $R_1$, $R_2$, $R_3$ and $R_4$ have the aforementioned values. Illustrative of the species included therein are:

N-[α-methyl[p-[3-(m-ethylphenyl)propoxy]phenyl]-methyl]-1,3-propanediamine,

N,N-dimethyl-N'-[]o-(3-phenylpropoxy)phenyl] methyl]-1,3-propanediamine,

N-ethyl,N-methyl-N'-[α-methyl[m-[3-(p-butyl-phenyl)propoxy]phenyl]methyl]-1,3-propanediamine, and N,N-diethyl-N'-[α-methyl[p-(3-phenylpropoxy)-phenyl]methyl]-1,3-propanediamine.

The expression "pharmaceutically acceptable acid addition salts" refers to any non-toxic organic or inorganic acid addition salts of the base compounds represented by formula (I). Illustrative inorganic acids which form suitable salts include hydrochloric, hydrobromic, sulfuric and phosphoric acids as well as acid metal salts such as sodium monohydrogen orthophosphate and potassium hydrogen sulfate. Illustrative organic acids which form suitable salts include the mono, di and tricarboxylic acids. Illustrative of such acids are, for example, acetic, propionic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicyclic, 2-phenoxybenzoic and sulfonic acids such as methanesulfonic acid and 2-hydroxyethanesulfonic acid. Either the mono or the di-acid salts can be formed, and such salts can be utilized in either a hydrated or a substantially anhydrous form.

Illustrative of specific base compounds encompassed by formula (I) above are:

N-[[p-[(o-methylphenyl)methoxy]phenyl]methyl]-1,2-ethanediamine,

N,N-dimethyl-N'-[α-methyl[o-[2-(p-ethylphenyl)ethoxy]phenyl]methyl]-1,3-propanediamine, N-ethyl,N-methyl-N'-[α-propyl]p-]3-(m-propylphenyl)propoxy]phenyl]methyl]-1,3-propanediamine, N-[α-ethyl[m-[4-(p-t-butylphenyl]methyl]-N'-propyl-1,4-butanediamine, N,N-dipropyl-N'[α-isobutyl[p-[(p-butylphenoxy)ethoxy]phenyl]methyl]1,2-ethanediamine, N-[[o-(2-phenoxyethoxy)phenyl]methyl]-1,3-propanediamine, N-ethyl,N-methyl-N'-[α-ethyl[p-[3-(m-propylphenyl)propylsulfonyl]phenyl]methyl]-1,3-propanediamine, N-isobutyl-N'-[α-methyl[p-[4-(p-t-butylphenyl)butylsulfonyl]phenyl]methyl]-1,4-butanediamine, N-[α-isobutyl[p-[3-(p-butylphenoxy)propylsulfonyl]phenyl]methyl]-N',N'-dipropyl-1,2-ethanediamine, N-ethyl-N'[[o-[2-(phenoxyethyl)sulfonyl]phenyl]methyl]-1,3-propanediamine, and N-butyl-N'-[α-ethyl[p-[4-(m-isobutylphenoxy)butylsulfonyl]phenyl]methyl]-1,4-butanediamine.

The primary amines of the present invention, in which $R_1$ and $R_2$ are each hydrogen, are prepared in accordance with the following reaction scheme, in which the symbols $R_3$, $R_4$, X, Y, m and n have the values previously assigned:

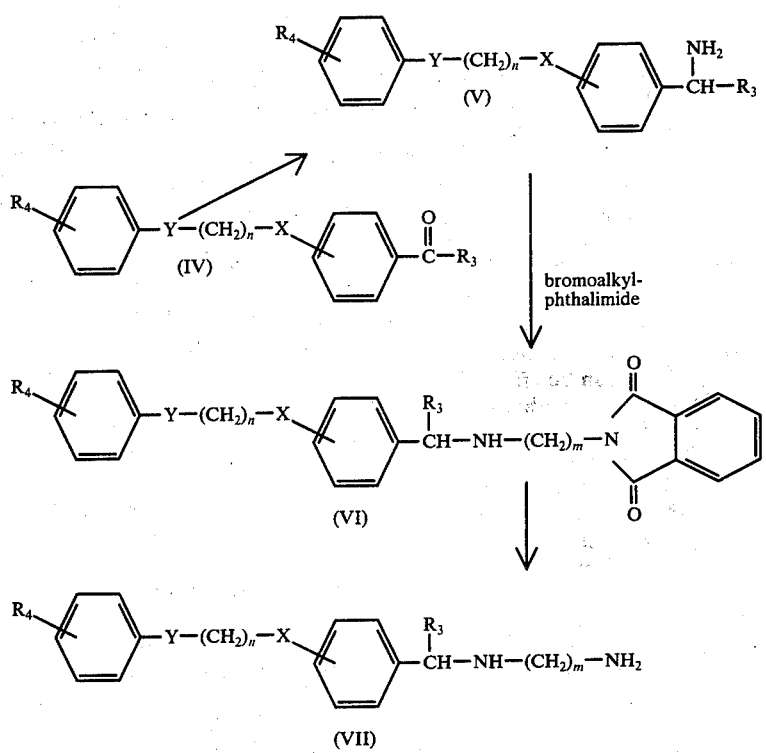

N-butyl-N'-[α-ethyl[p-[4-(m-isopropylphenoxy)butoxy]phenyl]methyl]-1,4-butanediamine, N-[[p-[(p-t-butylphenyl)methylthio]phenyl]methyl]-N',N'-diethyl-1,2-ethanediamine, N,N-dimethyl-N'-[α-propyl[o-[2-(m-propylphenyl)ethylthio]phenyl]methyl]1,3-propanediamine, N-ethyl,N-methyl-N'-[α-ethyl[p-[3-(p-ethylphenyl)propylthio]phenyl]methyl]-1,3-propanediamine, N-[α-butyl[p-[4-(o-methylphenyl)butylthio]phenyl]methyl]-N'-methyl-1,4-butanediamine, N-ethyl-N'-[α-isopropyl[p-[4-m-isopropylphenoxy)butylthio]phenyl]methyl]-1,2-ethanediamine, N,N-diethyl-N'-[[o-(2-phenoxyethylthio)phenyl]methyl]-1,3-propanediamine, N[α-ethyl[γ-[2-(p-butylphenoxy)ethylthio]phenyl]methyl]-1,4-butanediamine, N-ethyl-N'-[[p-[2-(o-methylphenyl)ethylsulfonyl]phenyl]methyl]-1,2-ethanediamine, N-[α-butyl[o-[2-(p-ethylphenyl)ethylsulfonyl[-phenyl]methyl]-N',N'-diethyl-1,3-propanediamine, The substituted α-alkyl-benzylamines (V) are obtained from their corresponding substituted phenyl alkyl ketones (IV) by a number of methods. One well-known procedure involves the Leuckart reation in which a substituted phenyl alkyl ketone (IV) is heated with a three to five-fold molar excess of ammonium formate at a temperature of from about 165° to 185° C. for a period of from about 4 to 16 hours. The reaction mixtue is vigorously stirred and hydrolyzed using concentrated hydrochloric acid to yield the corresponding α-alkyl-benzylamines (V). Alternatively, the substituted phenyl alkyl aldehydes or ketones (IV) are first converted to their oximes and then reduced to the α-alkyl-benzylamines (V), as for example, via catalytic hydrogenation with a platinum or rhodium/charcoal catalyst in an ethanol solvent.

The primary N-(substituted benzyl)alkanediamines (VIII) are prepared from the α-alkyl-benzylamines, (V), via the so-called Gabriel synthesis. Thus, the reaction of an α-alkyl-benzylamine (V) with a bromoalkylphthalimide, in which the alkyl group contains from 2 to 4 carbon atoms, in an aprotic solvent such as dimethylformamide at a temperature ranging from about 25° C. to about 100° C. results first in the formation of a phthalimide derivative (VI). Preferably, the reaction is conducted at a temperature of about 60° C. in the presence of a base, such as sodium or potassium carbonate. The phthalimide derivative is then converted to the desired primary N-(substituted benzyl) diamine (VII) by treatment either with hydrazine hydrate in refluxing ethanol, or by treatment with refluxing 6 N hydrochloric acid.

The secondary and tertiary amines of formula (I) are obtained directly from the corresponding substituted phenyl alkyl aldehydes or ketones (IV) via an acid-catalyzed condensation with unsymmetrically substituted diamines of the formula

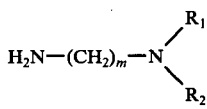

where either $R_1$ and/or $R_2$ are a loweralkyl group. The reaction is generally conducted in refluxing toluene or xylene under a Dean-Stark trap to remove water in the presence of an appropriate acid catalyst, as for example, toluenesulfonic acid. The resulting intermediate Schiff base so obtained is reduced with potassium borohydride in dimethylformamide or cold methanol (0°–20° C.).

The substituted phenyl alkyl ketones are prepared by condensing a hydroxyphenyl alkyl ketone with a phenylalkyl or phenoxyalkyl halide using procedures well-known to one skilled in the art. Thus, for example, condensation can be effected in the presence of a base such as potassium carbonate or sodium hydroxide with solvents such as dimethylformamide or amyl alcohol at reflux temperature.

The phenylalkylthio and phenoxyalkylthio ether side chain-containing compounds are prepared in a similar fashion using the corresponding phenylalkylthio- or phenoxyalkylthiophenyl alkyl ketones. These latter compounds can be prepared, for example, by reacting an o- or p-fluorophenyl alkyl ketone with a phenyl alkyl or phenoxyalkyl mercaptan. Typically, the reaction is conducted a refluxing dimethylformamide in the presence of potassium carbonate for a period of about 12 to 36 hours. Oxidation of the phenylalkylthiophenyl alkyl ketone or the phenoxyalkylthiophenyl alkyl ketone with potassium permanganate in acetic acid at a temperature of from about 50° to about 75° C. results in the formation of the corresponding sulfones.

It is to be noted that the N-(substituted benzyl) alkanediamines in which the symbol Y is oxygen and the symbol $n$ is the integer 1 have been specifically excluded by a proviso limitation for the symbol $n$. These compounds are difficult to prepare and furthermore are unstable due to the presence of 2 oxygen atoms or an oxygen and a sulfur atom on the same carbon atom.

The compounds of the present invention are antiviral agents. Preferably they are administered to an animal host to prevent or inhibit viral infections. The term host refers to any viable biological material or intact animal including humans which serves as a support means for virus replication. The host can be of animal or mammalian origin. Illustratively, such hosts include birds, mice, rats, guinea pigs, gerbils, ferrets, dogs, cats, cows, horses and humans. Other viable biological material such as used in the production of vaccines may also act as a host. Thus, tissue cultures prepared from organ tissues, such as mammalian kidney or lung tissue, as well as tissue cultures prepared from embryo tissue, such as obtained from amniotic cells or chick allantoic fluid, have been found to be useful hosts.

The treatment of virus infections for purposes of the present invention encompasses both the prevention and the inhibition of characteristic disease symptoms in a mammalian host susceptible to invasion by a pathogenic virus. Illustrative of mammalian virus infections which can be prevented or inhibited by the administration of the compounds of the present invention are infections caused by picornaviruses, such as encephalomycarditis virus; myxoviruses, such as influenza $A_2$ (Jap/305) virus; arboviruses, such as Semliki Forest virus; the herpes group of viruses, including herpes simplex; and the poxviruses, as for example vaccinia IHD. Thus, for example, the compounds of the present invention when administered orally or subcutaneously to mice in varying doses either shortly prior or subsequent to a fatal inoculation of a neurotropic virus such as Semliki Forest virus, having a $LD_{50}$ anywhere from 5 to 50, delay or prevent completely the onset of death. Salts of these compounds are generally administered in compositions containing a 0.15% aqueous hydroxyethylcellulose vehicle, whereas the free base compounds are generally administered in compositions containing a 10% aqueous surfactant vehicle in order to help suspend the compound. In general, 10 mice are used for each treated group with an additional 20 mice serving as a control group. At the time of administration the test virus is titrated in order to determine the potency or $LD_{50}$ for the particular virus pool used as a challenge. The control animals are given a placebo containing the identical volume of vehicle without, of course, the active ingredient. Because of the lethal nature of the test system employed, the antiviral nature of the test compound is dramatically illustrated by a side by side comparison of the number of survivors of treated animals with that of the untreated control group of materials.

Respiratory viruses, such as influenza $A_2$ (Jap/305) virus, which are also lethal to the test animals is employed, are administered via intranasal instillation. Animals infected in this manner have the active ingredients administered and again a side by side comparison is made of the survivors of the animals treated with the untreated control animals.

Inexplicably, a mouse fatally infected with Semliki Forest virus or influenza virus occasionally survives without treatment. The reasons for this are not understood and may be due to some genetic factor or other natural defense mechanism not presented understood. For this reason the control group selected is of sufficient size as to statistically reduce to a negligible amount the influence of such a chance survivor upon the test results.

The vaccinia test virus is typical of the dermatotrophic type viruses which respond to treatment with compositions containing the compounds of the instant invention. The vaccinia virus generally produces a nonfatal infection in mice, producing characteristic tail lesions when the virus is subcutaneously administered to the tail of the mouse. The instant compounds are administered either orally or subcutaneously either prior to or subsequent to the vaccinia infection. Tail lesions are subjectively scored on the eighth day following infection against untreated animals which serve as a control group. The compounds of the present invention have been found to be effective in varying degrees against one or all of these test virus systems.

As previously indicated, the compounds of the present invention may be prophylactically administered in order to prevent the spread of contagious viral diseases or they may be therapeutically administered to a host already infected intended for their curative effect. When administered prophylactically, it is preferred that the administration be made within 0 to 96 hours prior to the infection of the host animal with a pathogenic virus. When the compounds of the present invention are administered for their curative effect, it is preferred that they are administered within about 1 or 2 days following infection of the host in order to obtain the maximum therapeutic effect.

The dosage to be administered will be dependent upon such parameters as the particular virus for which either treatment or prophylaxis is desired, the species of animal involved, its age, health, weight, the extent of infection, concurrent treatment, if any, frequency of treatment and the nature of the effect desired. A daily dose of the active ingredients will generally range from about 0.1 mg. to about 500 mg. per kg. of body weight. Illustratively, dosage levels of the administered active ingredients for intravenous treatment range from about 0.1 mg. to about 10 mg. per kg. of body weight; for intraperitoneal administration range from about 0.1 mg. to about 50 mg. per kg. of body weight; for subcutaneous administration range from about 0.1 mg. to about 250 mg. per kg. of body weight; for oral administration may be from about 0.1 mg. to about 500 mg. per kg. of body weight; for intranasal instillation range from about 0.1 mg. to about 10 mg. per kg. of body weight; and for aerosol inhalation therapy, the range is generally from about 0.1 mg. to about 10 mg. per kg. of body weight.

The compounds of the present invention are useful as anticoagulants. They affect the coagulation of blood by preventing the aggregation of blood platelets. Blood platelets play a dominant role in thrombotic conditions, both in the initial event and at the occlusive stage. Additionally, all of the compounds of the present invention suppress immune response reactions, particularly those which are cellularly-mediate.

The novel compounds described herein can also be administered in various different dosage unit forms, e.g., oral compositions such as tablets, capsules, dragees, lozenges, elixirs, emulsions, clear liquid solutions and suspension; parenteral compositions such as intramuscular, intravenous or intradermal preparations; and topical compositions, such as lotions, creams or ointments. The amounts of active ingredient contained in each dosage unit form will, of course, vary widely according to the particular dosage unit employed, the animal host being treated, and the nature of the treatment, i.e., whether prophylactic or therapeutic in nature. Thus, a particular dosage unit may contain from about 2.0 mg. to over 3.0 g. of active ingredient in addition to the pharmaceutical excipients contained therein.

The novel compounds described herein can be employed in conjunction or admixture with additional organic or inorganic pharmaceutical excipients. Suitable solid excipients include gelatin, lactose, starches, magnesium stearate and petrolatum. Suitable liquid excipients include water and alcohols such as ethanol, benzyl alcohol and the polyethylene alcohols either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.05% to about 20% by weight, and preferably from about 0.1% to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil.

A preferred method of administration for the compounds of the present invention is orally either in a solid dose form such as a tablet or capsule, or in a liquid dose form such as an elixir, suspension, emulsion or syrup. Ordinarily the active ingredient comprises from about 0.5 to about 10% by weight in an oral liquid composition. In such compositions, the pharmaceutical carrier is generally aqueous in nature, as for example, aromatic water, a sugar-based syrup or a pharmaceutical mucilage. For insoluble compounds suspending agents may be added as well as agents to control viscosity, as for example, magnesium aluminum silicate or carboxymethylcellulose. Buffers, preservatives, emulsifying agents and other excipients can also be added.

For parenteral administration such as intramuscular, intravenous or subcutaneous administration, the proportion of active ingredient ranges from 0.05 to about 20% by weight, and preferably from about 0.1 to about 10% by weight of the liquid composition. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. The concentration of active ingredient contained in these various parenteral dosage unit forms varies over a broad range and comprises anywhere from about 0.05% to about 20% by weight of the total formulation, the remaining component or components comprising excipients previously mentioned.

The active ingredients of the present invention can also be admixed directly with animal feeds or incorporated into the drinking water of animals. For most purposes, an amount of active ingredient is used which provides from about 0.0001 to about 0.1% and preferably, from about 0.001 to about 0.02% by weight of the active ingredient based upon the total weight of feed intake. The active ingredients can be admixed in animal feed concentrates, suitable for use by farmers or livestock growers for incorporation in appropriate amounts with the final animal feeds. These concentrates ordinarily comprise from about 0.5 to about 95% by weight of the active ingredient compounded with a finely divided solid carrier or flour, such as wheat, corn, soybean or cottonseed flour. Depending upon the particular animal to be fed, nutrients and fillers may also be added such as ground cereal, charcoal, fuller's earth, oyster shells and finely divided attapulgite or bentonite.

The active ingredients of the present invention can be packaged in a suitable pressurized container together with an aqueous or volatile propellant for use as an aerosol. A suitable discharge valve is fitted to an opening in the container from which the active ingredients may be conveniently dispensed in the form of a spray, liquid, ointment or foam. Additional adjuvants such as co-solvents, wetting agents and bactericides may be employed as necessary. Normally, the propellant used is a liquified gaseous compound, preferably a mixture of low molecular weight fluorinated hydrocarbons. These haloalkanes are preferred because of their compatibility with the active ingredients of the present invention, and because they are non-irritating when applied to skin surfaces. Other useful propellants include ethylene oxide, carbon dioxide, propane and nitrogen gas.

The invention described herein is more particularly illustrated by means of the following specific examples.

EXAMPLE 1 p-(4-Phenoxybutoxy)acetophenone

A mixture 100 grams (0.438 mole) of 4-phenoxybutyl bromide, 59.5 grams (0.438 mole) of p-hydroxyacetophenone, and 60.4 grams (0.438 mole) of potassium carbonate in approximately 200 milliliters of dry dimethylformamide, is stirred at its reflux temperature for a period of about 4 hours. The reaction mixture is cooled, water added, and the reaction product removed by filtration. The product is washed with a solution of 2 N sodium hydroxide, washed with water, and recrystallized twice from isopropyl alcohol to yield the desired p-(4-phenoxybutoxy) acetophenone having a m.p. of 104°–6° C.

Following essentially the same procedure but substituting 4-(p-t-butylphenoxy)butyl bromide for the 4-phenoxybutyl bromide above, results in the formation of 4-[p-(t-butylphenoxy)butoxy]acetophenone.

EXAMPLE 2 p-(3-Phenylpropoxy)benzaldehyde

A mixture of 183.2 grams (1.5 mole) of p-hydroxybenzaldehyde, 270.3 grams (1.35 mole) of 3-phenylpropyl bromide and 207.0 grams (1.5 mole) of potassium carbonate in approximately 1 liter of dry dimethylformamide is stirred at its reflux temperature for approximately 3.5 hours. The solution is allowed to cool, is poured into water and extracted with ether. The ether extract is washed with a solution of 2 N sodium hydroxide, followed by a saturated sodium chloride solution and dried over anhydrous sodium sulfate. The solvent is removed by evaporation and the desired p-(3-phenylpropyl)benzaldehyde is vacuum distilled at 197°–202° C. at 0.2 mm of pressure.

Following essentially the same procedure, but substituting o-hydroxyacetophenone, m-hydroxyacetophenone, and p-hydroxyacetophenone for the p-hydroxybenzaldehyde above, results in the formation of o-(3-phenylpropoxy)acetophenone (b.p. 173°–8° C. at 0.1 mm), m-(3-phenylpropoxy)acetophenone (b.p. 199°–201° C. at 0.2 mm) and p-(3-phenylpropoxy) acetophenone (m.p. 80°–1° C.), respectively.

Following essentially the same procedure, but substituting benzyl chloride for the 3-phenylpropylbromide above, results in the preparation of p-(phenylmethoxy)acetophenone having a melting point of 93°–4° C.

EXAMPLE 3 p-(3-Phenylpropylthio)acetophenone

A mixture of 174.6 grams (1.15 mole) of 3-phenylpropyl thiol, 158.8 grams (1.15 mole) of p-fluoroacetophenone and 158.8 grams (1.15 mole) of potassium carbonate in 500 ml. of dry dimethylformamide is stirred at its reflux temperature for approximately 24 hours. The reaction mixture is cooled, water added and extracted with methylene chloride. The extract is washed with water, a solution of 2 N sodium hydroxide, dried over anhydrous sodium sulfate and evaporated in vacuo. The residue is recrystallized from isopropyl alcohol to yield the desired p-(3-phenylpropylthio)acetophenone having a m.p. of 76°–8° C.

To 135.0 grams (0.5 mole) of p-(3-phenylpropylthio) acetophenone in 600 ml. of acetic acid at 35°–40° C. is added a solution of 119 grams (0.75 mole) of potassium permanganate contained in 1,900 ml. of water. The reaction mixture is stirred for a period of 1 hour, heated to 75° C. and permitted to cool with stirring. Sodium sulfite is added to the cooled reaction mixture to reduce excess potassium permanganate. The manganese dioxide is removed by filtration, washed with acetic acid, isopropyl alcohol and acetone. Water is added to the filtrate and the desired p-(3-phenylpropylsulfonyl)acetophenone removed by filtration and recrystallized from a mixture of acetone/isopropanol to yield a compound having a melting point of 118°–20° C.

EXAMPLE 4

N-methyl-N'-[α-methyl[m-(3-phenylpropoxy)phenyl]methyl]-1,3-propanediamine

A solution of 38.2 grams (0.15 mole) of m-(3-phenylpropoxy)acetophenone, 13.3 grams (0.15 mole) of N-methylpropanediamine, 100 mg. of toluenesulfonic acid in approximately 300 ml. of toluene is maintained at its reflux temperature for approximately 4 hours under a Dean-Stark trap until 4.8 ml. of water is collected. The reaction mixture is evaporated to dryness in vacuo. Potassium borohydride, 0.1 g. (0.15 mole), and 100 ml. of dry dimethylformamide are added. The mixture is stirred at room temperature overnight, water added and extracted with ether. The ether extract is re-extracted with a solution of 2 N hydrochloric acid, the acidic phase washed with ether and made alkaline with a solution of 2 N sodium hydroxide. The aqueous alkaline solution is extracted with ether, the ether extract washed with a saturated sodium chloride solution, dried over anhydrous sodium sulfate and evaporated in vacuo, leaving a residual oil. A solution of 18 ml. of concentrated hydrochloric acid in isopropanol is added and the desired N-methyl-N'-[α-methyl[m-(3-phenylpropoxy)phenyl]methyl]-1,3-propanediamine dihydrochloride is isolated and recrystallized from an isopropanol/water mixture to yield a compound having a m.p. of 220°–2° C.

Following essentially the same procedure, but substituting p-(3-phenylpropoxy)acetophenone, o-(3-phenylpropoxy) acetophenone, p-(4-phenylbutoxy)acetophenone, p-(3-phenylpropoxy)benzaldehyde, p-[3-(p-t-butylphenoxy)propoxy]acetophenone, and p-(phenylmethoxy)acetophenone for the m-(3-phenylpropoxy)acetophenone above results in the preparation of N-methyl-N'-[α-methyl[p-(3-phenylpropoxy)phenyl]methyl]-1,3-propanediamine (m.p. 215°–17° C., dec.), N-methyl-N'-[α-methyl[o-(3-phenylpropoxy)phenyl]methyl]-1,3-propanediamine (m.p. 206°-8° C.), N-methyl-N'-[α-methyl[p-(4-phenoxybutoxy) phenyl]methyl]-1,3-propanediamine (m.p. 207°-9° C.), N-methyl-N'-[[p-(3-phenylpropoxy)phenyl]methyl]-1,3-propanediamine (m.p. 268°-9° C.), N-[α-methyl[p-[3-(p-t-butylphenoxy)propoxy]phenyl]methyl]-N'-methyl-1,3-propanediamine (m.p. 192°-4° C.) and N-methyl-N'-[α-methyl[p-(phenylmethoxy)phenyl]methyl]-1,3-propanediamine (m.p. 229°-30° C.), as their dihydrochloride salts, respectively.

Following essentially the same procedure, but substituting N-isopropylpropanediamine, N,N-diethylpropanediamine and N,N-diethylethanediamine for the N-methylpropanediamine above results in the formation of N-isopropyl-N'-[α-methyl [p-(3-phenylpropoxy)phenyl]methyl]-1,3-propanediamine as the dihydrochloride salt (m.p. 239°-40° C.), N,N-diethyl-N'-[α-methyl[p-(3-phenylpropoxy)phenyl]methyl]-1,3-propanediamine as the dimaleate salt (m.p. 132°-4° C., dec.), and N,N-diethyl-N'-[α-methyl[p-(3-phenylpropoxy)phenyl]methyl]-1,2-ethanediamine as the dimaleate salt (m.p. 90°-4° C.), respectively.

Following essentially the same procedure but substituting ethyl m-(3-phenylpropoxy)phenyl ketone, propyl p-[(o-methyl)phenylmethoxy]phenyl ketone and butyl p-(4-phenoxybutoxy)phenyl ketone for the m-(3-phenylpropoxy)acetophenone above results in the formation of N-[α-ethyl[m-(3-phenylpropoxy)phenyl]methyl]-N'-methyl-1,3-propanediamine, N-methyl-N'-[α-propyl[p-[(o-methylphenyl)methoxy]phenyl]methyl]-1,3-propanediamine, and N-[α-butyl[p-(4-phenoxybutoxy)phenyl]methyl]-N'-methyl-1,3-propanediamine as their dihydrochloride salts, respectively.

EXAMPLE 5

N-Methyl-N'-[α-methyl[p-(3-phenylpropylthio)phenyl]methyl]-1,3-propanediamine

A solution of 4.6 grams (0.15 mole) of p-(3-phenylpropylthio)acetophenone, 13.3 grams of N-methylpropanediamine, and a catalytic amount of toluenesulfonic acid in approximately 300 ml. of toluene is maintained at its reflux temperature under a Dean-Stark trap for approximately 4 hours until 4.7 ml. of water is collected. The reaction mixture is evaporated to dryness in vacuo, and 8.1 grams (0.15 mole) of potassium borohydride and 100 ml. of dry dimethylformamide are added. The reaction mixture is stirred overnight at room temperature, water added and extracted with ether. The ether extract is re-extracted with a 2 N hydrochloric acid solution and the aqueous layer made alkaline with a solution of 2 N sodium hydroxide. The aqueous alkaline solution is extracted with ether, the ether extract washed with a saturated solution of sodium chloride, dried over anhydrous sodium sulfate, and evaporated to dryness. Approximately 17 ml. of concentrated hydrochloric acid contained in isopropanol is added and the residue so obtained recrystallized from a mixture of isopropanol/water to yield the desired N-methyl-N'-[α-methyl[p-(3-phenylpropylthio)phenyl]methyl]-1,3-propanediamine as the dihydrochloride salt having a m.p. of 220°-3° C.

Following essentially the same procedure, but substituting o-(phenylmethylthio)acetophenone, m-(2-phenylethylthio) acetophenone and p-(4-phenylbutylthio)acetophenone for the p-(3-phenylpropylthio)acetophenone above results in the formation of N-methyl-N'-[α-methyl[o-(phenylmethylthio) phenyl]methyl]-1,3-propanediamine, N-methyl-N'-[methyl[m-(2-phenylethylthio)phenyl]methyl]-1,3-propanediamine, and N-methyl-N'-[α-methyl[p-(4-phenylbutylthio)phenyl]methyl]-1,3-propanediamine as their dihydrochloride salts, respectively.

EXAMPLE 6

N-Methyl-N'-[α-methyl[p-(3-phenylpropylsulfonyl)phenyl]methyl]-1,3-propanediamine A solution of 30.2 grams (0.1 mole) of p-(3-phenylpropylsulfonyl)acetophenone, 8.8 grams (0.1 mole) of N-methyl-propanediamine, 100 mg. of toluenesulfonic acid and approximately 200 ml. of toluene is maintained at its reflux temperature for approximately 4 hours under a Dean-Stark trap until 1.7 ml. of water is collected. The reaction mixture is evaporated to dryness in vacuo, and 5.4 grams (0.1 mole) of potassium borohydride in dry dimethylformamide is added. The reaction mixture is stirred at room temperature overnight, water added and extracted into ether. The ether extract is reextracted with a solution of 2 N hydrochloric acid, the aqueous layer is made alkaline with a solution of 2 N sodium hydroxide and re-extracted into ether. The ether extract is washed with a saturated solution of sodium chloride, dried over anhydrous sodium sulfate, evaporated to dryness in vacuo, and 14.5 ml. of concentrated hydrochloric acid in a solution of isopropanol is added. The solid residue so obtained is recrystallized from isopropanol to yield N-methyl-N'-[α-methyl[p-(3-phenylpropylsulfonyl)phenyl]methyl]-1,3-propanediamine as the dihydrochloride salt having a m.p. of 194°-7° C.

EXAMPLE 7

N-[α-Methyl[p-(3-phenylpropoxy)phenyl]methyl]-1,3-propanediamine

A mixture of 50.0 grams (0.197 mole) of p-(3-phenylpropoxy)acetophenone, prepared in accordance with the procedure of Example 2 and 49.5 grams (0.75 mole) of ammonium formate are heated with stirring to a temperature of 200°-10° C. for a period of 6 hours. The reaction mixture is cooled to about 100° C., approximately 150 ml. of water are added, and the reaction mixture is allowed to cool to room temperature overnight. The aqueous layer is decanted, 100 ml. of concentrated hydrochloric acid added and the mixture refluxed for a period of 1.5 hours. The reaction mixture is cooled, and the desired α-methyl-p-(3-phenylpropoxy)-benzylamine is collected by filtration, washed with benzene, and recrystallized from isopropanol to yield a product having a m.p. of 142°-5° C.

The above benzylamine, 23.0 grams (0.079 mole), is converted to its free base by the addition of sodium carbonate and subsequent extraction into ether. The free base, 19.6 grams, is added to 21.2 grams (0.079 mole) of bromopropylphthalimide and 100 ml. of dry dimethylformamide added. The reaction mixture is stirred at 80° C. overnight, poured into 1 liter of water and extracted into ether. The ether extract is washed with a saturated solution of sodium chloride, dried over anhydrous sodium sulfate, evaporated in vacuo and recrystallized from acetonitrile to yield the desired phthalimide derivative, having a m.p. of 76°-81° C.

The phthalimide derivative so prepared, 16.1 grams (0.0364 mole), hydrazine, 1.22 grams (0.0364 mole), and 200 ml. of absolute ethanol are heated to their reflux temperature for a period of about 6 hours. The reaction mixture is cooled, the solvent evaporated in vacuo, and the residue treated with 200 ml of water and approximately 45 ml. of a 10% hydrochloric acid solution at a temperature of 50°–60° C. for a period of 2 hours. On cooling, the precipitated phthalylhydrazide which forms is removed by filtration and the filtrate concentrated to an oil in vacuo. Recrystallization of the oily residue from a mixture of isopropanol/water results in the preparation of N-[α-methyl[p-(3-phenylpropoxy)phenyl]methyl]-1,3-propanediamine as the dihydrochloride salt having a m.p. of 221°–3° C.

Following essentially the same procedure, but substituting p-[4-(m-ethylphenyl)butoxy]acetophenone and p-(3-phenoxypropylthio)acetophenone for the p-(3-phenylpropoxy) acetophenone above results in the formation of N-[methyl[p-[4-(m-ethylphenyl)butoxy]phenyl]methyl]-1,3-propanediamine and N-[α-methyl[p-(3-phenoxypropylthio)phenyl]methyl]-1,3-propanediamine as their dihydrochloride salts, respectively.

EXAMPLE 8

The following Example is illustrative of the antiviral activity for the compounds of the present invention.

Thirty mice weighing approximately 20 gms. each are divided into two groups, a control group of 20 animals and a test group of 10 animals. All of the animals are challenged with a fatal dose ($5LD_{50}$) of Semliki Forest virus. The test group of animals are tested both prophylactically and therapeutically using a parenteral composition containing N-methyl-N'-[α-methyl[p-(3-phenylpropoxy) phenyl]methyl]-1,3-propanediamine dihydrochloride as the active ingredient dissolved in a solution of a 0.15% aqueous hydroxyethylcellulose solution as the vehicle. The composition contains the active ingredient in an amount such that each dosage contains 0.25 ml. which is equivalent to a dose level of 25 mg. per kg. The control group receives a subcutaneous placebo containing the same volume of vehicle without the active ingredient. Observations over an 8 day period show the termination of 95% of the control animals within a period of from 6 to 8 days, with 80% of the treated groups surviving.

EXAMPLE 9

Preparation of a Capsule Formulation

An illustrative composition for hard gelatin capsules is as follows:

|     |                                                                      | Per Capsule |
| --- | -------------------------------------------------------------------- | ----------- |
| (a) | N-[α-methyl[p-(3-phenylpropoxy)phenyl]methyl]-1,3-propanediamine     | 200 mg      |
| (b) | Talc                                                                 | 35 mg       |

The formulation is prepared by passing the dry powders of both (a) and (b) through a fine mesh screen and mixing them well. The powder is then filled into No. O hard gelatin capsules at a net fill of 235 mg. per capsule.

In a similar fashion, a soft gelatin capsule is prepared in which the talc is omitted. The dry N-[α-methyl [p-(3-phenylpropoxy)phenyl]methyl]-1,3-propanediamine powder can be filled directly as a granulation, slug or compressed tablet into a rotary dye or plate mold in which the soft gelatin capsule is formed.

EXAMPLE 10

Preparation of a Tablet Formulation

An illustrative composition for tablets is as follows:

|     |                                                                              | Per Tablet |
| --- | ---------------------------------------------------------------------------- | ---------- |
| (a) | N-methyl-N'-[α-methyl[m-(3-phenylpropoxy)phenyl]methyl]-1,3-propanediamine   | 100 mg     |
| (b) | Wheat starch                                                                 | 15 mg      |
| (c) | Lactose                                                                      | 33.5 mg.   |
| (d) | Magnesium stearate                                                           | 1.5 mg.    |

The granulation obtained upon mixing lactose, starch and granulated starch paste is dried, screened and mixed with the active ingredient and magnesium stearate. The mixture is compressed into tablets weighing 150 milligrams each.

EXAMPLE 11

Preparation of Parenteral Formulation

An illustrative composition for a parenteral injection injection is the following emulsion:

| Each ml. Contains | Ingredients                                                                  | Amount     |
| ----------------- | ---------------------------------------------------------------------------- | ---------- |
| 50 mg             | N-methyl-N'-[α-methyl[p-(3-phenylpropylsulfonyl)phenyl]methyl]-1,3-propanediamine | 1.000 g    |
| 100 mg            | Polyoxyethylene sorbitan monooleate                                          | 2.000 g    |
| 0.0064 mg         | Sodium chloride                                                              | 0.128 g    |
|                   | Water for injection, q.s.                                                    | 20.000 ml  |

The parenteral composition is prepared by dissolving 0.64 g. of sodium chloride in 100 ml. of water for injection, mixing the polyoxyethylene sorbitan monooleate with the N-methyl-N'-[α-methyl[p-(3-phenylpropylsulfonyl)phenyl]methyl]-1,3-propanediamine, adding a sufficient solution of the sodium chloride in water to the active ingredient and polyoxyethylene sorbitan monooleate to bring the volume to 20 ml., shaking the mixture, and finally autoclaving the mixture for 20 minutes at 110° C., at 15 p.s.i.g. steam pressure. The composition can be dispensed either in a single ampule for subsequent use in multiple dosage or in groups of 10 and 20 ampules for a single dosage administration.

We claim:

1. An N-(substituted benzyl)alkanediamine having the formula:

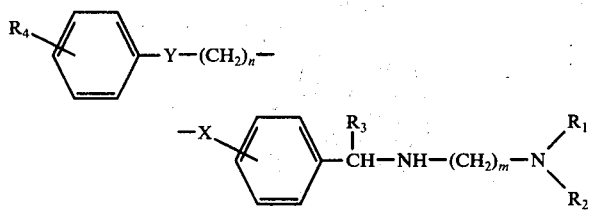

wherein
  $R_1$, $R_2$, $R_3$ and $R_4$ are each selected from the group consisting of hydrogen and loweralkyl having 1 to 4 carbon atoms;
  X is selected from the group consisting of oxygen, sulfur and $SO_2$;
  Y is oxygen or a sigma bond;

m is an integer of from 2 to 4;

n is an integer of from 1 to 4 with the proviso that when Y is oxygen, then n cannot be 1; and the pharmaceutically acceptable acid addition salts thereof.

2. A compound according to claim 1 wherein Y is a sigma bond and m is the integer 3.

3. A compound according to claim 2 wherein X is oxygen.

4. A compound of claim 1 which is N-[α-methyl[p-(3-phenylpropoxy)phenyl]methyl]-1,3-propanediamine.

5. A compound of claim 1 which is N-methyl-N'-[α-methyl [m-(3-phenylpropoxy)phenyl]methyl]-1,3-propanediamine.

6. A compound of claim 1 which is N-methyl-N'-[α-methyl[p-(3-phenylpropylsulfonyl)phenyl]methyl]-1,3-propanediamine 7. A method of treating a host susceptible to invasion by pathogenic viral agents caused by viruses which comprises administering from 0.1 milligram to 500 milligrams per kilogram of body weight per day of an N-(substituted benzyl)alkanediamine of claim 1.

8. A pharmaceutical composition in dosage unit form comprising from 2 milligrams to 3 grams of an N-(substituted benzyl)alkanediamine of claim 1 and a pharmaceutical carrier.

9. An oral dosage unit of a pharmaceutical composition comprising from 2 milligrams to 3 grams of an N-(substituted benzyl)alkanediamine of claim 1 and a pharmaceutical carrier.

* * * * *